(12) United States Patent
Bagaoisan et al.

(10) Patent No.: US 6,355,016 B1
(45) Date of Patent: Mar. 12, 2002

(54) CATHETER CORE WIRE

(75) Inventors: Celso J. Bagaoisan, Union City; Ketan P. Muni, San Jose; Gholam-Reza Zadno-Azizi, Newark; Sivette Lam, San Jose; Juan T. Domingo, Union City; Isaac J. Kim, San Jose; Samuel L. Omaleki, Morgan Hill; Jefferey C. Bleam, Boulder Creek, all of CA (US)

(73) Assignee: Medtronic PercuSurge, Inc., Sunnyvale, CA (US)

( * ) Notice: Subject to any disclaimer, the term of this patent is extended or adjusted under 35 U.S.C. 154(b) by 0 days.

(21) Appl. No.: 09/253,971

(22) Filed: Feb. 22, 1999

Related U.S. Application Data

(63) Continuation-in-part of application No. 09/026,357, filed on Feb. 19, 1998, now Pat. No. 6,190,332, and a continuation-in-part of application No. 08/813,024, filed on Mar. 6, 1997, now abandoned.

(51) Int. Cl.⁷ .............................................. A61M 29/00
(52) U.S. Cl. ................... 604/103.09; 604/526; 604/528
(58) Field of Search ........................... 604/95.01, 95.05, 604/96.01, 97.01, 102.02, 103, 264, 164.01, 164.03, 164.13, 103.09, 525, 526, 528

(56) References Cited

U.S. PATENT DOCUMENTS

| 3,144,868 A | 8/1964 | Jascalevich |
| 4,445,892 A | 5/1984 | Hussein et al. |
| 4,468,216 A | 8/1984 | Muto |

(List continued on next page.)

FOREIGN PATENT DOCUMENTS

| EP | 0 631 792 A1 | 12/1989 |
| EP | 0 442 480 A1 | 2/1991 |
| EP | 0 661 073 A1 | 7/1995 |
| EP | 0 770 404 A1 | 5/1997 |
| EP | 0770404 | 5/1997 |
| EP | 0 812 828 | 12/1997 |
| EP | 0 868 924 A2 | 10/1998 |
| WO | WO 92/00775 | 1/1992 |
| WO | WO 96/07351 | 3/1996 |
| WO | WO96/13295 | 5/1996 |
| WO | WO 97/11735 | 4/1997 |
| WO | WO 96/15824 | 5/1997 |
| WO | 9615824 | 5/1997 |
| WO | 0 784 991 A2 | 7/1997 |
| WO | WO 97/44084 | 11/1997 |
| WO | WO 98/55173 | 12/1998 |
| WO | WO 99/19018 | 4/1999 |

*Primary Examiner*—Anhtuan T. Nguyen
*Assistant Examiner*—Ann Y. Lam
(74) *Attorney, Agent, or Firm*—Knobbe, Martens, Olson & Bear, LLP

(57) ABSTRACT

Disclosed herein is an improved core wire for use in a medical catheter. In one aspect, a tapering core wire is incorporated into the distal end of a catheter. The catheter has a tubular body. Both ends of an inflatable balloon are mounted to the tubular body. The core wire extends from the distal end of the tubular body. In one embodiment, substantially all of the taper of the core wire occurs in the extending portion of the core wire over a length of at least 15 mm but no more than 60 mm. In another aspect, a core wire with a shapeable tip and method of manufacturing the same are provided. A core wire previously made superelastic is subject to additional processing to remove its superelasticity thereby allowing the material to be shapeable to aid in advancing the core wire through a blood vessel or other body cavities. In another aspect of the present invention, a method is provided for securing the core wire to the distal end of an elongated catheter tubular body. The tubular body is mechanically crimped onto the core wire to secure the core wire in place. This crimping method has been found to increase the strength of the bond between the core wire and the catheter tube so that greater pull force is required to break the core wire off from the catheter.

19 Claims, 10 Drawing Sheets

U.S. PATENT DOCUMENTS

| | | | |
|---|---|---|---|
| 4,511,354 A | 4/1985 | Sterling | |
| 4,573,470 A | 3/1986 | Samson et al. | |
| 4,573,966 A | 3/1986 | Weikl et al. | |
| 4,616,652 A | 10/1986 | Simpson | |
| 4,616,653 A | 10/1986 | Samson et al. | |
| 4,723,936 A | 2/1988 | Buchbinder et al. | |
| 4,748,982 A | 6/1988 | Horzewski et al. | |
| 4,763,654 A | 8/1988 | Jang | |
| 4,771,778 A | 9/1988 | Mar | |
| 4,793,350 A | 12/1988 | Mar et al. | |
| 4,838,268 A | 6/1989 | Keith et al. | |
| 4,846,174 A | 7/1989 | Willard et al. | |
| 4,846,193 A | 7/1989 | Tremulis et al. | |
| 4,917,088 A | 4/1990 | Crittenden | |
| 4,943,278 A | 7/1990 | Euteneuer et al. | |
| 4,946,466 A | 8/1990 | Binchuk et al. | |
| 4,964,409 A | 10/1990 | Tremulis | |
| 4,976,690 A * | 12/1990 | Solar et al. | |
| 4,976,720 A | 12/1990 | Machold et al. | |
| 4,984,581 A | 1/1991 | Stice | |
| 4,998,917 A | 3/1991 | Gaiser et al. | |
| 5,042,985 A | 8/1991 | Elliott et al. | |
| 5,059,178 A | 10/1991 | Ya | |
| 5,159,937 A | 11/1992 | Tremulis | |
| 5,163,906 A | 11/1992 | Ahmadi | |
| 5,167,239 A | 12/1992 | Cohen et al. | |
| 5,211,636 A | 5/1993 | Mische | |
| RE34,466 E | 12/1993 | Taylor et al. | |
| 5,312,340 A | 5/1994 | Keith | |
| 5,322,508 A | 6/1994 | Viera | |
| 5,341,818 A | 8/1994 | Abrams et al. | |
| 5,368,049 A | 11/1994 | Raman et al. | |
| 5,378,236 A * | 1/1995 | Seifert | |
| 5,385,152 A * | 1/1995 | Abele et al. | 128/772 |
| 5,387,225 A | 2/1995 | Euteneuer et al. | |
| 5,411,476 A | 5/1995 | Abrams et al. | |
| 5,417,658 A | 5/1995 | Loney et al. | |
| 5,423,742 A | 6/1995 | Theron | |
| 5,439,000 A | 8/1995 | Gunderson et al. | |
| 5,449,343 A | 9/1995 | Samson et al. | |
| 5,451,209 A | 9/1995 | Ainsworth et al. | |
| 5,462,529 A | 10/1995 | Simpson et al. | |
| 5,470,315 A * | 11/1995 | Adams | 604/96 |
| 5,486,183 A | 1/1996 | Middleman et al. | |
| 5,499,973 A * | 3/1996 | Saab | 604/96 |
| 5,500,180 A | 3/1996 | Anderson et al. | |
| 5,522,818 A * | 6/1996 | Keith et al. | 604/102 |
| 5,558,643 A | 9/1996 | Samson et al. | |
| 5,567,203 A | 10/1996 | Euteneuer et al. | |
| 5,601,572 A | 2/1997 | Middleman et al. | |
| 5,637,089 A | 6/1997 | Abrams et al. | |
| 5,640,970 A | 6/1997 | Arenas et al. | |
| 5,706,826 A | 1/1998 | Schwager | |
| 5,782,741 A | 7/1998 | Bradshaw et al. | |
| 5,876,356 A | 3/1999 | Viera et al. | |
| 6,048,329 A * | 4/2000 | Thompson et al. | 604/95 |
| 6,050,972 A * | 4/2000 | Zadno-Azizi et al. | 604/97 |

* cited by examiner

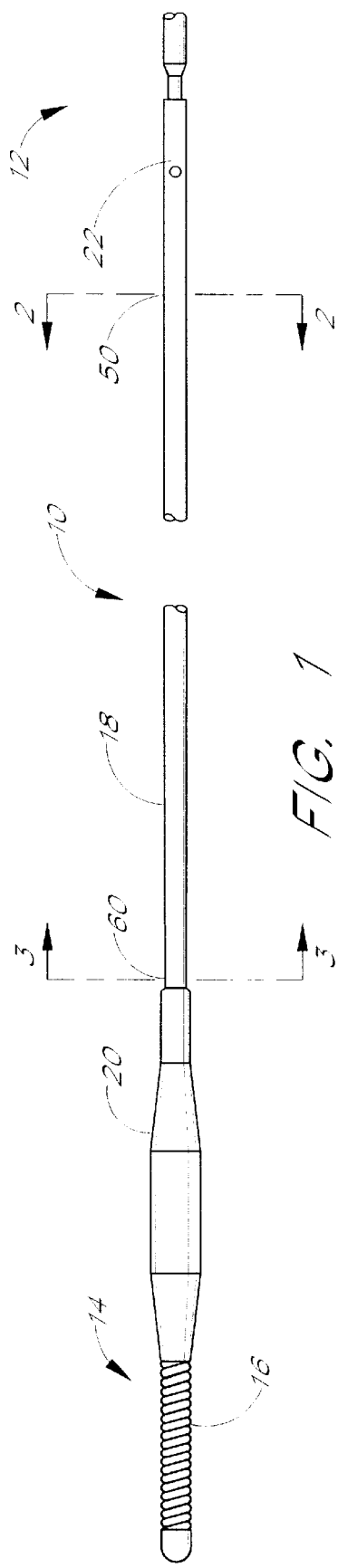
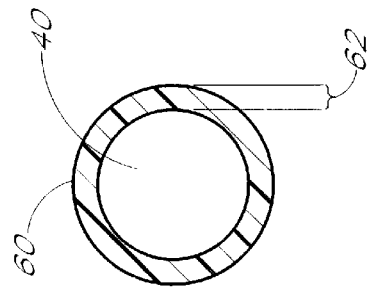
FIG. 1
FIG. 3
FIG. 2

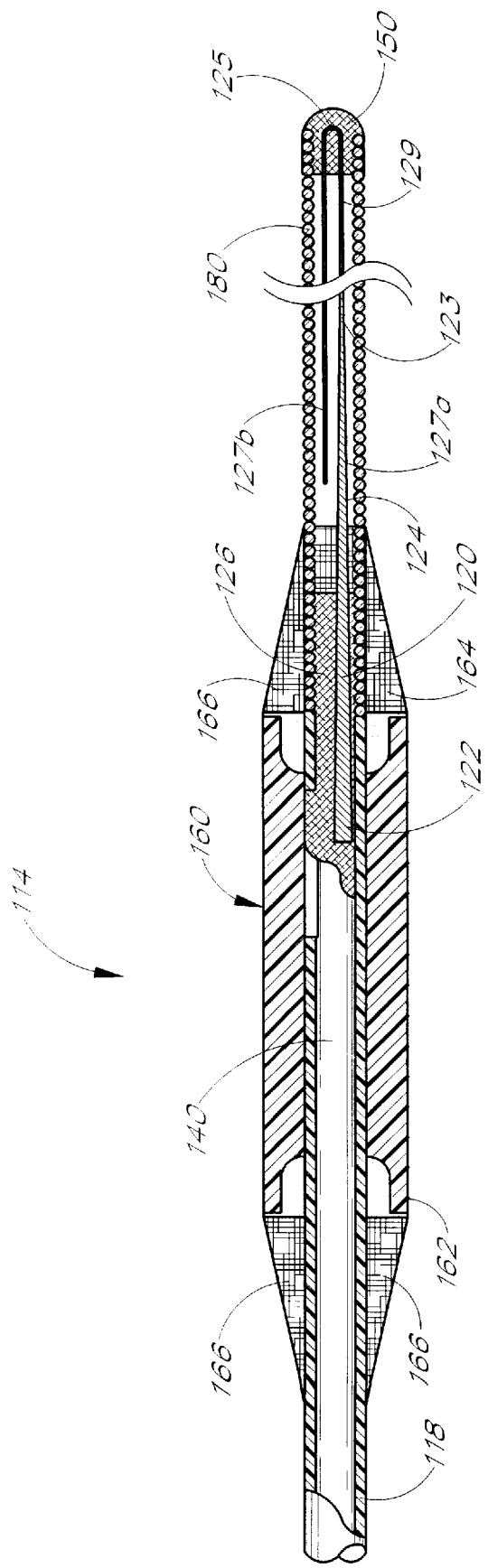

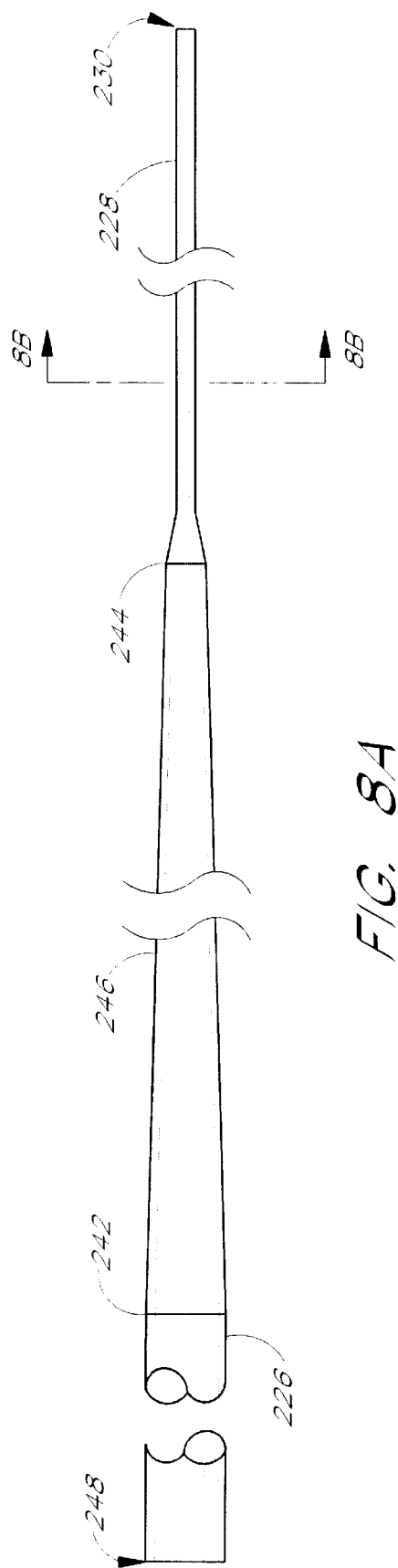
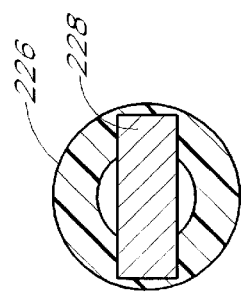
FIG. 8A
FIG. 8B

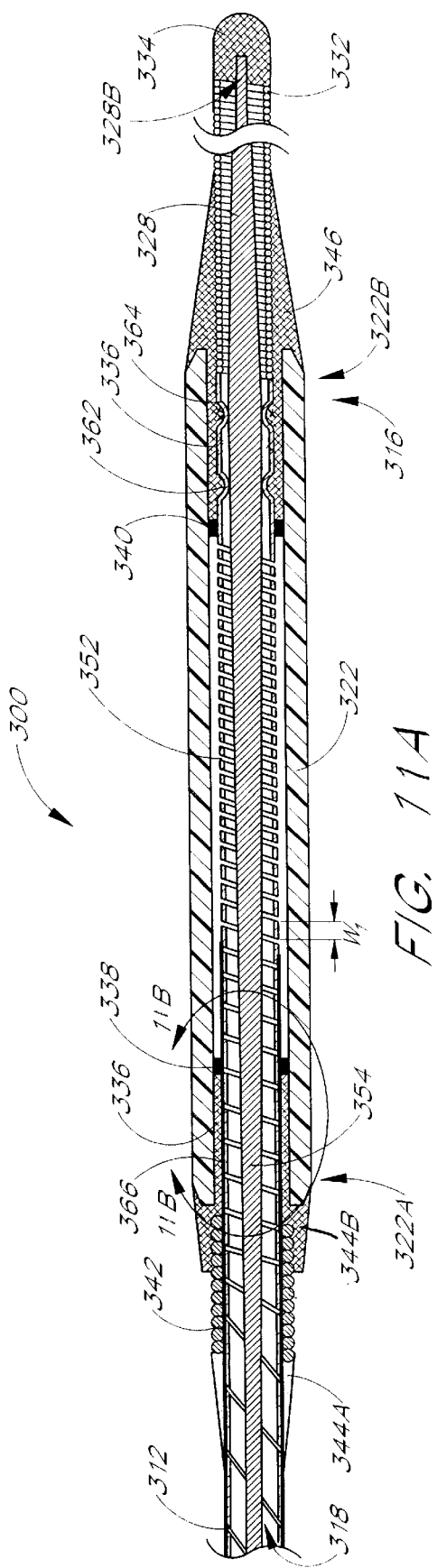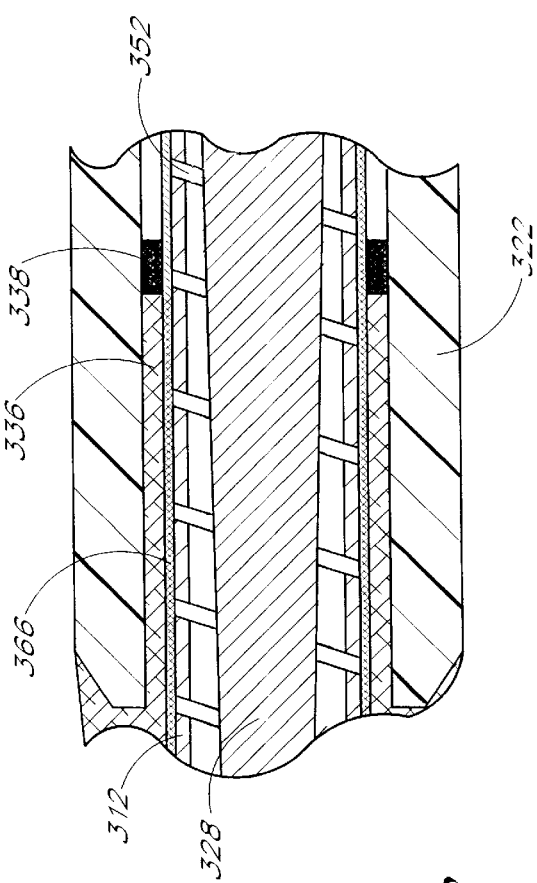

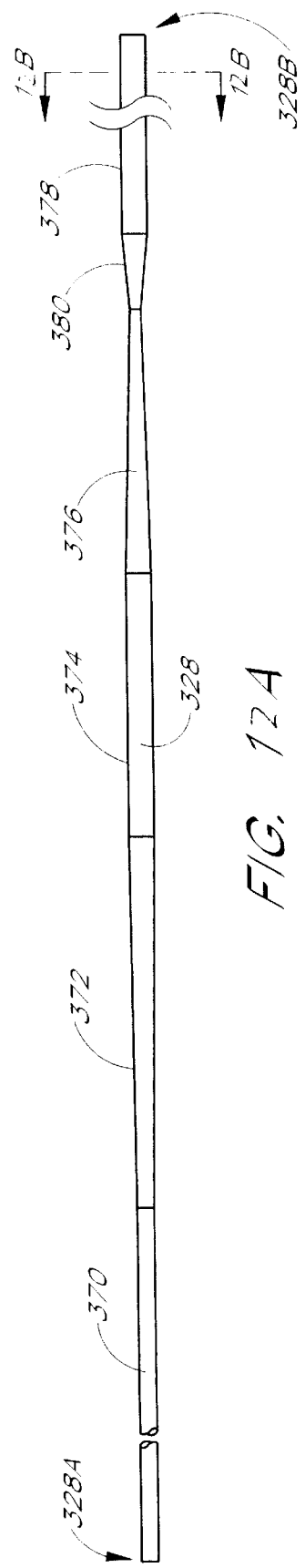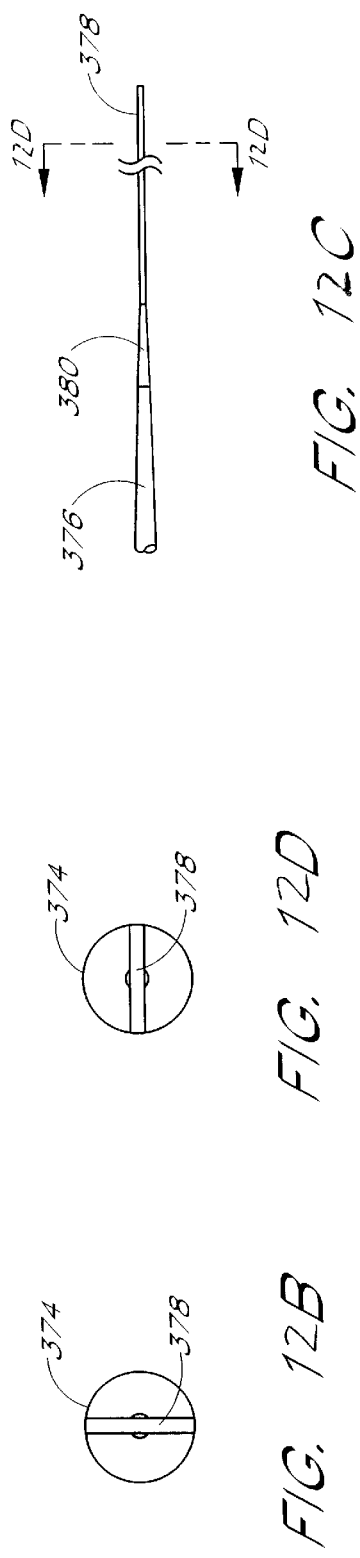
FIG. 12A
FIG. 12B
FIG. 12C
FIG. 12D

CATHETER CORE WIRE

CROSS-REFERENCE TO RELATED APPLICATIONS

The present application is a continuation-in-part of application Ser. No. 08/813,024, filed Mar. 6, 1997, now abandoned, and application Ser. No. 09/026,357, filed Feb. 19, 1998, now U.S. Pat. No. 6,190,332 both of which are hereby incorporated by reference in their entirety.

BACKGROUND OF THE INVENTION

1. Field of the Invention

The present invention relates generally to medical devices, and in particular, to core wires used in catheters and the like.

2. Description of the Related Art

Medical catheters, such as guidewires and balloon catheters, have been proven efficacious in treating a wide variety of blood vessel disorders. Moreover, these types of catheters have permitted clinicians to treat disorders with minimally invasive procedures that, in the past, would have required complex and perhaps life threatening surgeries. For example, balloon angioplasty is now a common procedure to alleviate stenotic lesions (i.e., clogged arteries) in blood vessels, thereby reducing the need for heart bypass operations.

Because medical catheters must be passed through a tortuous blood vessel network to reach the intended treatment site, it is desirable that the catheters be fairly flexible, especially at the distal end. However, the distal end must not be so flexible that it tends to bend back upon itself when the clinician advances the catheter distal end through the patient.

One method of imparting desired flexibility characteristics to a catheter has been to incorporate a "core wire" into the distal end of the catheter. A core wire is a wire that extends from the distal end of a catheter body, providing structural support to the distal end to prevent bend backs or kinks during catheter advancement. Furthermore, the core wire is also flexible, such that the catheter distal end may navigate tortuous blood vessel networks or other body cavities.

Previously known catheter core wires are of complex construction, requiring multiple manufacturing steps to incorporate the core wire into the catheter. This increases manufacturing costs of the catheter, which ultimately are passed on to hospitals and patients. Moreover, previously known core wires may not be sufficiently flexible. Accordingly, there exists a need for catheter core wires that are easier to manufacture, and which possess the desired flexibility profiles.

Previously known catheter core wires also may not be sufficiently rigid at the very distal tip of the wire. In particular, catheter core wires are commonly formed of superelastic materials such as NiTi alloys which exhibit an elastic response when subject to stress. Superelasticity refers to the ability of a material to undergo deformation and to return to its original configuration without being permanently or "plastically" deformed. This superelasticity, often referred to as transformational superelasticity, exhibits itself as the parent crystal structure of the material as it transforms into a different crystal structure. In superelastic materials the parent crystal structure is known as the austenitic phase and the product crystal structure is known as the martensitic phase. Such formed martensite is termed stress-induced martensite.

While superelasticity may be desirable for the majority of the core wire, superelasticity at the very distal tip of the core wire creates the problem that the tip will not be shapeable. Shapeability is desirable so that a doctor or other person inserting the catheter into the body can shape the tip into a form advantageous for insertion and navigation through the body. If the tip of the core wire is superelastic, the material cannot be shaped.

An additional problem with previously known core wires is that they may not be securely attached to the distal end of the catheter. What is needed is a method to make the connection between the catheter and the core wire secure so that the stress of vascular navigation will not cause breakages.

SUMMARY OF THE INVENTION

The present invention addresses the needs raised above by providing a catheter core wire with improved flexibility and a simple and easily manufacturable design. In one aspect of the present invention, there is provided a catheter with a tubular body having a proximal end and a distal end. The tubular body has a lumen extending therethrough. An expandable member is mounted on the distal end of the tubular body. The expandable member has a proximal portion and a distal portion which are both mounted to the tubular body.

A core wire is inserted into the lumen at the distal end. The core wire has an end mounted within the lumen and an extending portion which extends from the distal end of the tubular body. The extending portion is tapered through a length of no more than 60 mm but at least 5 mm, preferably 60 to 15 mm, more preferably 50 to 15 mm, and optionally 35 to 15 mm.

In one aspect of the present invention, the core wire is tapered over a length of no more than 40 mm but at least 10 mm, and is made of a nitinol alloy or stainless steel. The core wire may have a first cross-sectional area at one end of the taper, and a second cross-sectional area at the other end of the taper, the first cross-sectional area being greater than the second cross-sectional area by at least 20%. In another embodiment, the first cross-sectional area is greater than the second cross-sectional area by at least 70%. In these embodiments, the extending portion may also have a region of constant cross-sectional area.

In another aspect of the present invention, there is provided a hollow guidewire formed from a hypotube having a proximal end and a distal end. The proximal end has a first wall thickness and the distal end has a second wall thickness. The first wall thickness is greater than the second wall thickness. An expandable member is mounted on the distal end of the hypotube, and there is a tapered core wire extending from the distal end of the hypotube. In one embodiment, the hypotube is made of nitinol, and the first wall thickness is 20% greater than the second wall thickness.

In another aspect of the present invention, there is provided a hollow guidewire, formed of a nitinol hypotube having a proximal end and a distal end. The nitinol hypotube has a lumen extending between the proximal and distal ends. An expandable member is mounted on the distal end. A core wire is inserted into the lumen at the distal end of the nitinol hypotube, and the distal end is crimped on the core wire to secure it within the lumen.

In another aspect of the present invention, there is provided a catheter having a tubular body. The tubular body has a proximal end and a distal end, and an irrigation lumen extending therethrough. An irrigation opening is on the distal end of the tubular body. The irrigation opening is in fluid communication with the irrigation lumen. A core wire has an end mounted within the lumen. The core wire has an extending portion which extends from the distal end of the tubular body, the extending portion being tapered through a length of no more than 60 mm but at least 5 mm.

In another aspect of the present invention, there is provided core wire with a shapeable tip and method of manufacturing the same. A core wire previously made superelastic is subject to additional processing to remove superelasticity from a distal tip, thereby allowing the material at the distal tip to be shapeable to aid in advancing the core wire through a blood vessel or other body cavities.

In one embodiment, the core wire is manufactured by first providing an elongate body of NiTi alloy or similar material. This elongate body is subject to a first cold working in the range of about 20 to 40%. A heat treatment in the range of about 300° to 600° C. for 10 seconds to 60 minutes is performed to impart superelasticity to the body. Following heat treatment, the distal end of the core wire is cold worked from about 10 to 50%, removing superelasticity from this end and producing a shapeable tip at the end of the core wire. The core wire that results is a flexible, superelastic body having a shapeable distal tip with no superelasticity.

Alternatively, once the NiTi is imparted with superelasticity, the distal end of the core wire can be removed of its superelasticity by an additional heat treatment. Heat treatments at temperatures of about 400–800° C. for extended periods of time will cause the material to lose its superelasticity at the distal end. Additionally, superelasticity can be imparted to the core wire by a solution treatment followed by aging process.

In another embodiment of the present invention, a method is provided for securing the core wire to the distal end of an elongated catheter tubular body. Conventional means for attaching a core wire to a catheter body is by soldering, which uses flux of hydrogen. NiTi alloys are susceptible to hydrogen embrittlement, which will in turn diminish the tensile strength of the material. Because of the stresses involved in advancing the catheter through a vessel network, it has been discovered that a core wire soldered to a catheter may break off during catheter advancement. In one aspect of the present method, the tubular body is mechanically crimped onto the core wire to secure the core wire in place. This crimping method has been found to increase the strength of the bond between the core wire and the catheter tube so that greater pull force is required to break the core wire off from the catheter.

In another aspect of the present invention, a medical catheter is provided comprising an elongate tubular body having a proximal end and a distal end and a lumen extending therethrough. An expandable member is mounted to the distal end of the tubular body. A core wire having a proximal taper and a distal taper extends from the distal end of the tubular body. In one preferred embodiment, the core wire has a section of substantially constant diameter between the proximal taper and distal taper that is crimped to the tubular body. The core wire preferably extends into the lumen at the distal end over a length of about 10 to 100 mm to provide additional structural support to the tubular body.

In another aspect of the present invention, a core wire is provided comprising an elongate body having a proximal end and a distal end and superelastic properties. A shapeable distal tip extends from the distal end of the elongate body. A proximally tapered transition section is provided between the distal end of the elongate body and the distal tip.

BRIEF DESCRIPTION OF THE DRAWINGS

FIG. 1 is a side view of a catheter incorporating the core wire in one embodiment of the present invention.

FIG. 2 is a cross-sectional view along lines 2—2 of FIG. 1.

FIG. 3 is a cross-sectional view along lines 3—3 of FIG. 1.

FIG. 4 is a longitudinal cross-sectional view of the distal end of a catheter having the core wire in one embodiment of the present invention.

FIG. 8A is a side view of the core wire manufactured in accordance with the preferred method of the present invention.

FIG. 8B is a cross-sectional view along line 8B—8B of the core wire of FIG. 8A.

FIG. 11A is a longitudinal cross-sectional view of a balloon catheter incorporating a multiple tapered core wire.

FIG. 11B is an enlarged view of the proximal end of the balloon of FIG. 11A.

FIGS. 12A–12D are side views of the core wire inserted into the hypotube of FIG. 11.

DETAILED DESCRIPTION OF THE PREFERRED EMBODIMENTS

Figure 5:
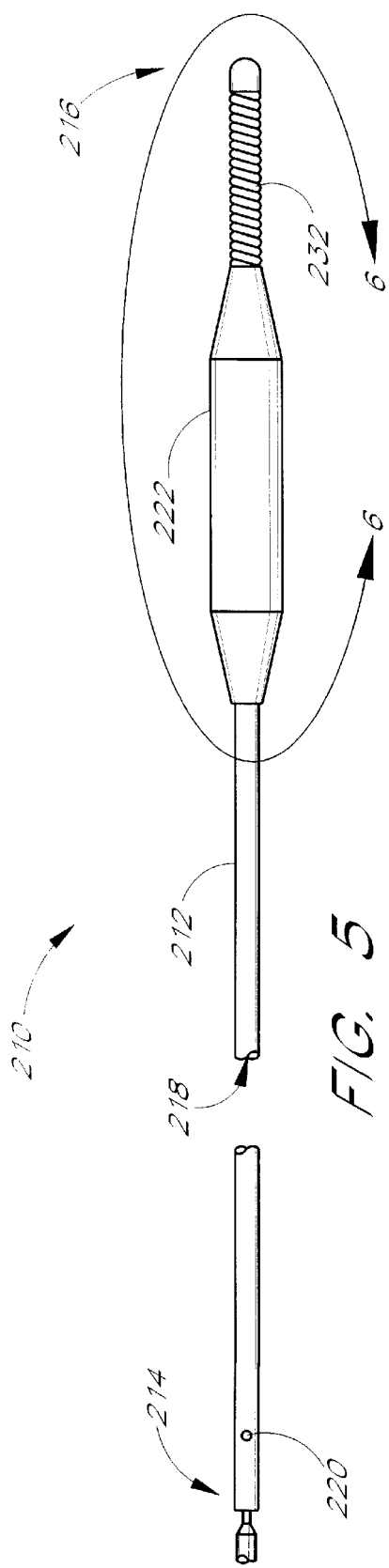
FIG. 5 is a side view of a catheter incorporating the core wire in a preferred embodiment of the present invention.

Referring to FIGS. 1 and 5, there are depicted catheters 10 and 210, respectively, incorporating core wires in accordance with the preferred embodiments of the present invention. Although the core wires are depicted and discussed in the context of being part of a simple occlusive device having a single lumen, it should be appreciated that the principles and aspects of the present invention are applicable to more complex occlusive devices having structures and functionalities not discussed herein. For example, the present inventors contemplate that the core wires of the present invention may be used in occlusive devices functioning as anchorable guide wires or filters. In addition, the core wires of the present invention are also applicable to catheters having other types of balloons, such as latex or silicone, or to catheters used for dilatation balloons, made of materials such as polyethylene terephthalate. Moreover, the cores wire of the present invention may also be adapted to other types of non-balloon catheters, such as irrigation catheters used in drug delivery or radiation therapy, or catheters carrying other types of expandable members, such as filters and meshes. The tip design of the core wire can also be applicable to ordinary guidewires. In this case the guidewire may be hollow or solid. The manner of adapting the core wires of the present invention to these various structures and functionalities will become readily apparent to those of skill in the art in view of the description which follows.

Occlusion Balloon Catheter And Core Wire

In the embodiment illustrated in FIG. 1, the core wire of the present invention is incorporated in an occlusion balloon catheter 10. It should be appreciated that the term "occlusion" refers to both partial and total occlusion. Catheter 10 generally comprises an elongate flexible tubular body 18 extending between a proximal control end 12 and a distal functional end 14. Tubular body 18 has a central lumen 40 which extends between ends 12 and 14. An inflation port 22 is provided on tubular body 18 near the proximal end. Inflation port 22 is in fluid communication with lumen 40, such that fluid passing through inflation port 22 into or out of lumen 40 may be used to inflate or deflate inflatable balloons in communication with lumen 40. Lumen 40 is sealed fluid tight at distal end 14. Inflation port 22 may be similar to existing female luer lock adapters or could be a removable valve at the end. Further details may be found in assignee's copending applications entitled LOW PROFILE CATHETER VALVE, Ser. No. 08/812,139, filed Mar. 6, 1997, abandoned, and LOW VOLUME SYRINGE AND METHOD OF INFLATING SURGICAL BALLOONS, Ser. No. 09/195,796, filed Nov. 19, 1998, abandoned, both of which are incorporated by reference in their entirety.

The length of tubular body 18 may be varied considerably depending upon the desired application. For example, where catheter 10 serves as a guidewire for other catheters in a conventional percutaneous transluminal coronary angioplasty procedure involving femoral artery access, tubular body 18 is comprised of hollow hypotube having a length in the range of from about 160 to about 320 centimeters with a length of about 180 centimeters being optimal for a single operator device and 300 centimeters for over the wire applications. Alternately, for a different treatment procedure, not requiring as long a length of tubular body 18, shorter lengths of tubular body 18 may be provided.

Tubular body 18 generally has a circular cross-sectional configuration with an outer diameter within the range of from about 0.008 inches to 0.14 inches. In many applications where catheter 10 is to be used as a guidewire for other catheters, the outer diameter of tubular body 18 ranges from 0.010 inches to 0.038 inches, and preferably is 0.018 inches in outer diameter or smaller. Non-circular cross-sectional configurations of lumen 40 can also be adapted for use with the present invention. For example, triangular, rectangular, oval, and other non-circular cross-sectional configurations are also easily incorporated for use with present invention, as will be appreciated by those of skill in the art.

Tubular body 18 has sufficient structural integrity, or "pushability," to permit catheter 10 to be advanced through vasculature to distal arterial locations without buckling or undesirable kinking of tubular body 18. It is also desirable for tubular body 18 to have the ability to transmit torque, such as in those embodiments where it may be desirable to rotate tubular body 18 after insertion into a patient. A variety of biocompatible materials, known by those of skill in the art to possess these properties and to be suitable for catheter manufacture, may be used to produce tubular body 18. For example, tubular body 18 may be made of stainless steel, or may be made of polymeric materials such as nylon, polyimide, polyamides, polyethylene or combinations thereof. In one preferred embodiment, the desired properties of structural integrity and torque transmission are achieved by forming tubular body 18 out of an alloy of titanium and nickel, commonly referred to as nitinol. In a more preferred embodiment, the nitinol alloy used to form tubular body 18 is comprised of about 50.8% nickel and the balance titanium, which is sold under the trade name TINEL (TM) by Memry Corporation. It has been found that a catheter tubular body having this composition of nickel and titanium exhibits an improved combination of flexibility and kink resistance in comparison to other materials. Further details may be found in our co-pending application entitled HOLLOW MEDICAL WIRES AND METHODS OF CONSTRUCTING SAME, Ser. No. 08/812,876, filed Mar. 6, 1997, now U.S. Pat. No. 6,068,623, the entirety of which is incorporated by reference.

As shown in FIGS. 1–3, tubular body 18 may be formed of a hollow nitinol hypotube. Hollow nitinol hypotube 18 has a proximal portion 50 having a first wall thickness 52 and a distal portion 60 having a second wall thickness 62. Wall thickness 52 is at least 5% greater, preferably at least 20% greater, more preferably at least 40% greater, and may be as much as 60% greater or more than wall thickness 62. For example, where proximal portion 50 has a wall thickness of 0.002", distal portion 60 has a wall thickness of 0.0013. The wall thickness may be reduced at the distal end of the tubular body from points starting about 30 cm proximal of balloon 20 to points just distal to the balloon. For example, wall thickness may be reduced starting at points 1 cm, 5 cm, 10 cm, 20 cm or 30 cm proximal of balloon 20. Alternatively, wall thickening may be reduced starting at a point just distal to balloon 20.

In one embodiment, the wall thickness is reduced by removing wall material from the outer diameter of the tubular body, while maintaining lumen diameter 40 constant, so as to introduce a gradual taper in the tubular body. The wall thickness of the nitinol tubular body may be reduced by any means known to those of skill in the art, such as grinding, swaging, or etching.

Referring to FIG. 4, there is depicted a catheter distal end 114. Distal end 114 is provided with a tapering core wire 120 at the distal end of a tubular body 118. Tubular body 118 may have differing wall thicknesses along its length, as described previously. Core wire 120 is preferably formed of a shape memory alloy, such as nitinol, but may also be formed of other materials, such as stainless steel. A proximal end 122 of core wire 120 is inserted into a lumen 140 of tubular body 118 and is attached thereto. End 122 may be secured to lumen 140 by any means known to those of skill in the art, such as adhesives. Particularly preferred adhesives for attachment are cyanoacrylates of the type sold under the trade name LOCTITE. Other adhesives, such as metal to metal bond adhesives may also be used. Core wire end 122 may also be secured within lumen 140 by welding or soldering.

Alternately in another preferred embodiment, proximal end 122 of core wire 120 may be secured within lumen 140 by crimping tubular body I118 such that the interior surface of tubular body 118 defining lumen 140 contacts proximal end 122 and firmly secures it within lumen 140. Preferably, tubular body 118 is crimped at least two points, and more preferably at three or more points, to secure proximal end 122 within lumen 140. In those embodiments where tubular body 118 is made of nitinol, sufficient crimping pressure must be exerted upon tubular body 118 to overcome the elastic response of nitinol. Generally, this requires exertion of sufficient pressure to deform the nitinol tubular body 118 by 9% or more. For a nitinol tubular body 118 having an outer diameter of 0.014 inches and an inner diameter of 0.0095 inches to be crimped over a nitinol core wire end 122 having an outer diameter of 0.009 inches, it has been found that a pressure of 120 ksi is sufficient. Other pressures may also be used, provided that they are sufficient to cause tubular body 118 to securely contact core wire 122, but not so great as to unduly deform tubular body 118.

Core wire 120 may range in length from about 20 mm to about 200 mm or more, preferably from 25 mm to 50 mm, and, for most occlusive device applications, is typically about 40 mm. Extending portion 124 may have a length which varies from about 15 mm to about 95 mm or more, preferably 20 mm to 45 mm, and optimally about 35 mm.

Core wire 120 has a portion 124 which extends from tubular body 118. Extending portion 124 tapers from a larger cross-sectional diameter to a smaller cross-sectional diameter. Preferably, substantially all of the tapering of core wire 120 occurs in extending portion 124. In one preferred embodiment, the cross-sectional area of extending portion 124 decreases by at least 20%, preferably by 60%, more preferably by 70%, and optimally by 85%, from a point 126 just distal of the termination of tubular body 118 to a second, more distal point 123 on extending portion 124. For example, where a core wire end 122 has a cross-sectional area of about 0.00003 $in^2$ and is inserted to a catheter tubular body having a lumen with an inner diameter of about 0.0093" core wire 120 preferably tapers from a cross-sectional area of about 0.0003 $in^2$ at point 126 to about 0.0000049 $in^2$ at point 123. A region of constant cross-sectional area 129 may be provided to core wire 120 at points distal to portion 123. In this and other embodiments, catheter tubular body 118 may have varying wall thickness, as described above.

As illustrated in FIG. 4, an inflatable balloon 160 is mounted on tubular body 118. Balloon 160 has a proximal portion 162 and a distal portion 164. Proximal portion 162 and distal portion 164 are both secured to the outer surface of tubular body 118. Balloon 160 may be secured to tubular body 118 by any means known to those of skill in the art, such as adhesives or heat bonding. In one preferred embodiment, balloon 160 is a compliant balloon formed out of a material comprising a block copolymer of styrene-ethylene-butadiene-styrene or styrene-ethylene-butylene-styrene (SEBS), as described below. Tapers 166 may be provided proximally and distally of balloon 160.

Core wire 120 may be provided with a bend 125, such that core wire 120 bends back upon itself to form portions 127a and 127b, as shown in FIG. 4. Bend 125 and portions 127a and 127b facilitate shaping of the distal extremity of a guidewire incorporating core wire 120 during its use. In one preferred embodiment, core wire portions 127a and 127b are of approximately the same length. Bend 125 is secured within a hemispherical solder bump or protrusion 150 which is carried by the distal extremity of a coil 180 formed of a suitable radiopaque material such as gold, platinum or a platinum alloy. Coil 180 can have a suitable outside diameter which corresponds to the outer diameter of tubular body 118, and can have a suitable length ranging from about 2 to about 10 cm. For example, where tubular body 118 has an outer diameter of 0.014 inches, and core wire 120 has a length of 37 mm, coil 180 may have a length of about 35 mm.

Coil 180 is secured to the distal end of tubular body 118 by suitable means such as an adhesive or by soldering or brazing. One preferred adhesive type for connecting coil 180 to tubular body 118 is cyanoacrylate, although, as will be appreciated by those of skill in the art, other similar adhesives adopted to form metal to metal bonds may also be used.

Balloon Formation

Expandable members, such as balloons used on catheters incorporating the core wire may be formed out of any material used to manufacture inflatable catheter balloons, such as latex, silicone, or inelastic materials, such as polyethylene terephthalate, or combinations of material comprising a block copolymer of styrene-ethylene-butylene-styrene (SEBS). It has been found that SEBS resins can be used to form catheter balloons with improved elasticity in comparison to other compliant balloon materials. Preferred SEBS resins for balloons may be purchased under the trade name C-FLEX, sold by Consolidated Polymer Technologies. In particular, the C-FLEX (TM) resin grade R70-050-000 is presently preferred.

As a first step in the balloon formation process, the selected SEBS resin is extruded to form a tube which will subsequently be shaped into a balloon. The resin may be extruded to form tubes having a variety of different internal and outer diameters, as can be readily appreciated by those of skill in the art. It is preferable, however, that the inner diameter of the extruded tubing be no more than about 120% greater and preferably no more than about 80% greater than the outer diameter of the catheter tubular body to which the finished balloon will be mounted. For example, where the outer diameter of tubular body 18 is about 0.014 inches, as is preferable for many hollow guidewire applications, the inner diameter of this extruded SEBS tubing is preferably from about 0.016 inches to about 0.030 inches, more preferably 0.020 inches to about 0.027 inches, and optimally about 0.025 inches. The outer diameter of the extruded SEBS tube is preferably about 0.035 inches to about 0.060 inches, more preferably 0.042 inches to about 0.058 inches, and optimally is 0.053 inches (for a 3.5–4.5 mm balloon).

Any suitable one inch extrusion apparatus may be used to form the extruded SEBS tubes. For example, balloons may be formed from tubing extruded on a 1" Harrel extruder, set to a draw down ratio of from about 1 to about 1.4, more preferably to a draw down ratio of about 1 to about 1.2.

It is important to monitor the extrusion process to ensure that the resulting tubing has substantially uniform inner and outer diameters along its length. In other words, uniform concentricity of the resulting extruded tube is very important. One important variable that needs to be monitored and controlled is the amount of tension which is applied to the tubing during the extrusion process. It is important not to apply too much tension, so that the tubing keeps proper dimensions along its length. For example, for extrusion of tubing having an inner diameter of about 0.025 inches and an outer diameter of about 0.053 inches, applied tension during extension preferably does not exceed 4 oz.

Extrusion tension can be controlled by a variety of means, as is known to those of skill in the art. For example, extrusion tension can be controlled by using hand extrusion, by low tension pullers, by low tension winders, or by other means known to those of skill in the art.

The extruded SEBS tubing has an inner diameter much larger than the outer diameter of the catheter tubular body, such that the tubing may not be directly mounted to the tubular body to form a balloon. Accordingly, the inner diameter of the SEBS tubing must be reduced before the SEBS tube may be mounted to the catheter tubular body as a balloon.

Thus, one important step in forming the balloons involves reducing both the inner and outer diameter of the SEBS tubes by a pre-stretching process. Advantageously, the pre-stretching process not only reduces the inner and outer diameters such that the SEBS tubing may be mounted to a catheter tubular body as a balloon, but also results in a finished compliant balloon which exhibits reduced longitudinal expansion upon inflation. Indeed, it has been discovered that the prestretching process is capable of reducing longitudinal expansion of finished SEBS balloons by from about 20% to about 50%.

The pre-stretching process generally. comprises longitudinally stretching the extruded SEBS tube by at least 200%, such that substantially all lengthwise deformation of the SEBS tube occurs along a line parallel to the longitudinal axis of the SEBS tube. In other words, the tube is stretched lengthwise while controlling the stretching process variables to minimize curvature or other bends in the tube. Preferably, the extruded SEBS tube is stretched by at least 400%, more preferably by at least 600%, and optimally by at least 900%, such that the inner diameter of the SEBS tube decreases from its starting size to about 0.002–0.003 inches greater than the outer diameter of the catheter tubular body to which the extruded tube is to be mounted as a balloon. Furthermore, the pre-stretching process also preferably reduces the outer diameter of the SEBS tube from its starting size, to an outer diameter which is at least 15% smaller, more preferably 25% smaller, and optimally at least 30% smaller than the starting outer diameter size. For example, where the starting inner diameter of an extruded SEBS tube is about 0.025 inches, and the starting outer diameter of the tube is 0.053 inches, the tube may be stretched so that it length increases by about 600–700%, so that the resulting inner diameter of the tube is about 0.016 inches and the resulting outer diameter is about 0.035 inches. A stretched tube with these dimensions is preferably mounted to the embodiment of the tubular body 18 having an outer diameter of about 0.014 inches to form a balloon.

As is readily appreciated by those of skill in the art, where the outer diameter of the tube is reduced more than the inner diameter, the thickness of the tube also decreases. Preferably the thickness is reduced by at least 10%, more preferably by at least 20%, and optimally by at least 30%. Greater reductions in thickness may also result from the pre-stretching process and still function, depending upon the grade of SEBS resin and the stretching conditions used. The manner of adapting these different resin grades and stretching conditions will be apparent to those of skill in the art in view of the description herein.

The pre-stretching process is preferably carried out at temperature which facilitates the stretching without contributing to any undesirable bending of the tube. For most grades of SEBS, temperatures of between 0° to about 90° C. are preferred. Temperatures lower than this generally require the application of increased longitudinal force to carry out the stretching process, resulting in increased risk of nonuniform stretching or bending of the resulting tube. Moreover, at temperatures greater than about 90° C., the SEBS block copolymer used to form the tubing tends to soften considerably, such that gravitational force may introduce unwanted bend or curvature in the tube. Optimally, stretching is done at about 25–30° C.

The stretching rate also has an important effect on the properties of the resulting balloon. Preferably, the SEBS tubing is stretched at a rate of from about 0.5 cm per min to about 50 cm per minute, more preferably at a rate of less than 30 cm/min., and optimally is stretched at a rate of 10 cm inches per minute at room temperature. Stretching rates greater than the maximum amount may result in undesirable residual elongation. After the pre-stretching process is completed, the stretched SEBS tubing is preferably permitted to settle for a period of about 10–15 seconds, prior to removal from the stretching apparatus.

Once the pre-stretching process is completed, the stretched tubing is preferably cut to appropriate balloon length within two hours of the stretching, otherwise tube relaxation may occur which adversely affects the dimensions of the stretched tube. Cutting may be performed by any means known to those of skill in the art. One preferred cutting process comprises inserting a stainless steel mandrel into a polyamide tube, and then inserting the mandrel/polyamide tube combination into the lumen of the stretched SEBS tube. The stainless steel mandrel is then removed, leaving the polyamide tube within the stretched SEBS tube. The polyamide tube provides structural support to the SEBS tube during the cutting process, facilitating the formation of straight cut edges. For example, for a stretched SEBS tube having an inner diameter of about 0.016 inches and an outer diameter of about 0.035 inches, a stainless steel mandrel having an outer diameter of 0.013 inches is inserted into a polyamide tube having an inner diameter of 0.0145 inches and an outer diameter of 0.0155 inches. The combination is then inserted into the stretched SEBS tube, and the stainless steel mandrel is removed. A standard cutting tool, such as a razor blade is then used to cut through the SEBS tubing and the polyamide tubing into segments having lengths of approximately 9 mm. After the cutting is completed, the polyamide tubing is removed.

The stretched and cut pieces of SEBS tubing may then be bonded to catheter tubular bodies to form compliant inflatable balloons. Conventional balloon bonding techniques may be used to mount the SEBS balloons to catheter tubular bodies. Such techniques include adhesive bonding and heat bonding, as known to those of skill in the art. In one preferred embodiment where the catheter tubular body comprises nitinol, a primer is first applied to the inner surface of each end of the SEBS tube to improve the bonding of the SEBS tube to nitinol. One suitable primer found useful for the priming step is 7701 LOCTITE, sold by Loctite Corp. However, as will be appreciated by those of skill in the art, other primers may also be used. The primer is preferably applied only to the inner surface of the SEBS tube at its ends, and more preferably, each end inner surface is primed for a distance of about 2 mm extending inward.

After the priming step, the primed tubing is slid over the catheter tubular body to the appropriate balloon position, such as over a fill hole in communication with an inflation lumen. Each end of the SEBS tubing is then mounted to the catheter tubular body to form a fluid tight seal. In a preferred embodiment, a cyanoacrylate adhesive is used to bond the SEBS tubing to the nitinol catheter tubular body. One preferred cyanoacrylate is LOCTITE 4011, sold by Loctite Corp. When using the LOCTITE 4011 adhesive, however, it is important to control the humidity of the surrounding environment, such that the humidity is maintained at at least 35% to 40%.

While adhesive bonding is taking place, clamps are preferably placed adjacent to the working area of the balloon to prevent adhesive flow inward. For example, if a 9 mm SEBS tube is bonded to a catheter tubular body along 2 mm at each end, clamps are placed slightly inward of the 2 mm mark, so that 5 mm of tubing is not bonded to the tubular body, and may function as a balloon.

After the SEBS tube has been bonded to the catheter tubular body to form a balloon, and the adhesive has set, tapers are preferably formed on the balloon to facilitate unhindered movement within a patient. Tapers may be added by conventional means known to those of skill in the art, such as adhesive bonding of the tapered parts separately to the catheter after the balloon has been attached. Alternately, tapers can be formed by adhesives which are applied to the balloon. In addition, it is possible to mold the balloon with a taper and then attach it.

The Preferred Guidewires and Catheters

Figure 6:
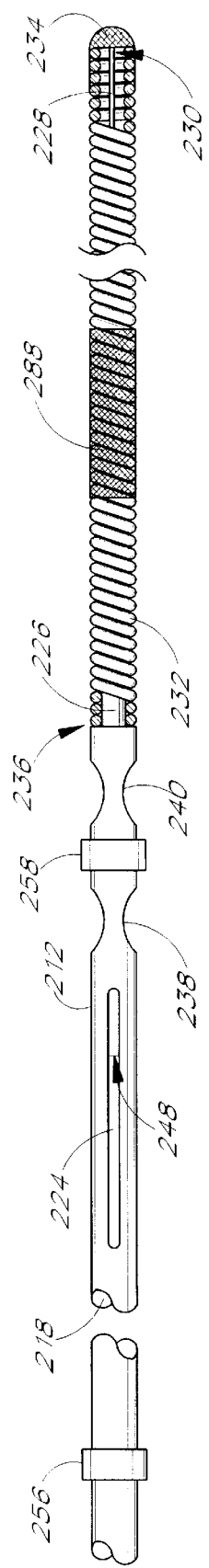
FIG. 6 is a longitudinal partial sectional view of a distal portion of the catheter implementing the preferred core wire before balloon mounting.

FIGS. 5 and 6 illustrate a preferred guidewire or similar catheter incorporating a preferred embodiment of the core wire of the present invention. The manufacture and construction of the core wire is described in more detail below in connection with FIGS. 7 and 8, respectively. Referring to FIG. 5, catheter 210 generally comprises an elongate flexible tubular body 212 extending between a proximal control end 214, corresponding to a proximal section of the tubular body 212, and a distal functional end 216, corresponding to a distal section of tubular body 212. Tubular body 212 has a central lumen 218 which extends between ends 214 and 216. An inflation port 220 is provided on tubular body 212 near the proximal end 214. Inflation port 220 is in fluid communication with lumen 218, such that fluid passing through inflation port 220 into or out of lumen 218 may be used to inflate or deflate inflatable balloons in communication with lumen 218. Lumen 218 is sealed fluid tight at distal end 16. Inflation port 220 may be similar to existing female luer lock adapters or would be a removable valve at the end. Further details may be found in assignee's co-pending applications entitled LOW PROFILE CATHETER VALVE AND INFLATION ADAPTER, Ser. No. 08/975,723, filed Nov. 20, 1997, now U.S. Pat. No. 6,050,972, and LOW VOLUME SYRINGE AND METHOD OF INFLATING SURGICAL BALLOONS, Ser. No. 09/195,796, filed Nov. 19, 1998, abandoned, both of which are incorporated by reference in their entirety.

The length of tubular body 212 may be varied considerably depending upon the desired application. For example, where catheter 210 serves as a guidewire for other catheters in a conventional percutaneous transluminal coronary angioplasty procedure involving femoral artery access, tubular body 212 is comprised of a hollow hypotube having a length in the range of from about 160 to about 320 centimeters with a length of about 180 centimeters being optimal for a single operator device and 300 centimeters for over the wire applications. Alternately, for a different treatment procedure, not requiring as long a length of tubular body 212, shorter lengths of tubular body 212 may be provided. Moreover, the catheter 210 may comprise a solid body rather than a hollow hypotube.

Tubular body 212 generally has a circular cross-sectional configuration with an outer diameter within the range of from about 0.008 inches to 0.14 inches. In many applications where catheter 210 is to be used as a guidewire for other catheters, the outer diameter of tubular body 212 ranges from 0.010 inches to 0.038 inches, and preferably is 0.014 to 0.018 inches in outer diameter or smaller. Non-circular cross-sectional configurations of lumen 218 can also be adapted for use with the present invention. For example, triangular, rectangular, oval, and other non-circular cross-sectional configurations are also easily incorporated for use with the present invention, as will be appreciated by those of skill in the art.

Tubular body 212 has sufficient structural integrity, or "pushability," to permit catheter 210 to be advanced through vasculature to distal arterial locations without buckling or undesirable kinking of tubular body 212. It is also desirable for tubular body 212 to have the ability to transmit torque, such as in those embodiments where it may be desirable to rotate tubular body 212 after insertion into a patient. A variety of biocompatible materials, known by those of skill in the art to possess these properties and to be suitable for catheter manufacture, may be used to produce tubular body 212. For example, tubular body 212 may be made of a stainless steel material such as ELGILOY (TM), or may be made of polymeric materials such as nylon, polyimide, polyarnides, polyethylene or combinations thereof. In one preferred embodiment, the desired properties of structural integrity and torque transmission are achieved by forming tubular body 212 out of an alloy of titanium and nickel, commonly referred to as nitinol. In a more preferred embodiment, the nitinol alloy used to form tubular body 212 is comprised of about 50.8% nickel and the balance titanium, which is sold under the trade name TINEL (TM) by Memry Corporation. It has been found that a catheter tubular body having this composition of nickel and titanium exhibits an improved combination of flexibility and kink resistance in comparison to other materials. Further details may be found in assignee's co-pending applications entitled HOLLOW MEDICAL WIRES AND METHODS OF CONSTRUCTING SAME, application Ser. No. 08/812,876, filed Mar. 6, 1997, now U.S. Pat. No. 6,068,623, and SHAFT FOR MEDICAL CATHETERS, application Ser. No. 09/025,105, filed Feb. 19, 1998, now U.S. Pat. No. 6,228,072, both of which are hereby incorporated by reference.

As illustrated in FIG. 5, an expandable member such as an inflatable balloon 222 is mounted on tubular body 212. Balloon 222 may be secured to tubular body 212 by any means known to those skilled in the art, such as adhesives or heat bonding. In one preferred embodiment, balloon 222 is a compliant balloon formed out of a material comprising a block polymer of styrene-ethylene-butylene-styrene, as disclosed in assignee's co-pending application entitled BALLOON CATHETER AND METHOD OF MANUFACTURE, application Ser. No. 09/026,225, filed on Feb. 19, 1998, the entirety of which is incorporated by reference.

Referring to FIG. 6, a distal portion of tubular body 212 is shown before mounting of the balloon 222. A notch 224 is provided in the tubular body 212 to allow fluid communication between the inner lumen 218 and the balloon 222 (not shown) attached to the tubular body 212. An elongate body or core wire 226 is provided at the distal end 236 of the tubular body 212, and extends within the inner lumen 218 of the tubular body 212 to a position visible through the notch 224. Adhesive stops 256, 258 are provided on tubular body 212 to prevent adhesive bonding of the balloon 222 past the location of the stops, as disclosed in the above-referenced application BALLOON CATHETER AND METHOD OF MANUFACTURE, application Ser. No. 09/026,225, filed on Feb. 19, 1998.

Core wire 226 is preferably formed of a shape memory alloy, such as nitinol, but may also be formed of other materials, such as stainless steel. The core wire 226 extends from a proximal end 248, corresponding to a proximal section of the core wire, to a distal end 230, corresponding to a distal section of the core wire. The core wire 226 has a flattened tip 228 at its distal end 230, as described in more detail below in connection with FIGS. 7 and 8. Core wire 226 may range in length from about 20 mm to 100 mm, or more preferably from about 25 mm to 50 mm, and for most occlusive device applications, is typically about 40 mm. In one preferred embodiment, the length of the core wire is about 37 mm. Flattened tip 228 extends from the distal end 230 for a length between about 5 and 10 mm, and more preferably about 7.5 mm.

As shown in FIG. 6, coil 232 is provided around the core wire 226 and extends substantially along the entire length of core wire 226, from the distal end 230 of core wire 226 to the distal end 236 of tubular body 212. Coil 232 is soldered at the distal tip 230 of the core wire 226 forming a ball 234. Coil 232 is secured to the distal end 236 of tubular body 212 by suitable means such as soldering, brazing, or by an adhesive, as described in more detail below. One preferred adhesive type for connecting coil 232 to tubular body 212 is a cyanoacrylate such as LOCTITE 4011, although, as will be appreciated by those of skill in the art, other similar adhesives adopted to form metal to metal bonds may also be used. Coil 232 is formed of a suitable radiopaque material such as gold, platinum or a platinum alloy. Coil 232 can have a suitable outside diameter which corresponds to the outer diameter of tubular body 212, and can have a suitable length ranging from about 10 to about 50 mm. For example, where tubular body 212 has an outer diameter of 0.014 inches, and core wire 226 has a length of 37 mm, coil 232 may have a length of about 35 mm.

As described in more detail below, the core wire 226 and the coil 232 are formed into a subassembly prior to attachment to tubular body 212. Once the coil 232 is attached to the core wire, the proximal end 248 of core wire 226 is inserted into tubular body 212 at distal end 236. Two crimps 238 and 240 are provided near the distal end 236 of the tubular body 212 to secure the core wire 226 to the tubular body. The crimps are preferably located in a location between the notch 224 and the distal tip 236 of the tubular body 212. The crimps are preferably located a distance 0.5 to 1.5 mm apart, and more preferably, about 1.0 mm apart. The more distal crimp 240 preferably is located about 0.5 mm from the distal tip 236 of tubular body 212.

Manufacture of the Core Wire

Figure 7A:
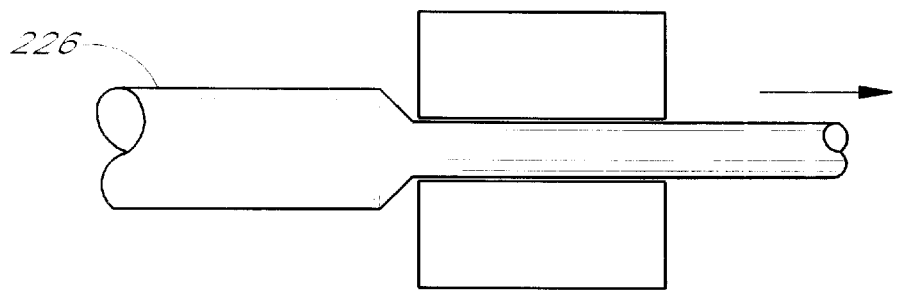
FIG. 7A is a schematic view of a first process step for producing the core wire.

Referring to FIGS. 7A, 7B, 7C and 7D, the core wire 226 can be manufactured by facilitating various thermal and/or mechanical treatments. The alloy comprising the core wire is preferably a NiTi or other superelastic alloy with a length preferably from about 20 to 200 mm, more preferably about 25 to 50 mm, and most preferably of about 37 mm. The alloy can be made superelastic by cold working the material and then heat treating the alloy. In the first step, a cold work can be performed to reduce the core wire diameter. Various facilitating instruments such as swager, metal extrusion and drawing equipment can be utilized to provide cold work. In a preferred embodiment, the core wire 226 is shaped by wire drawing the material at a preferred cold work range of about 20–40%, as shown in FIG. 7A.

Figure 7B:
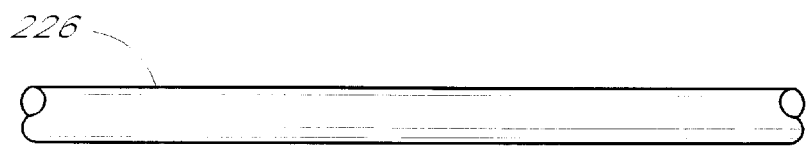
FIG. 7B is a schematic view of a second process step for producing the core wire.

In step two of the process shown in FIG. 7B, following the cold work the core wire is preferably heat treated at a temperature range between about 300 and 600° C. This heat treatment can preferably be done in a salt bath, such as potassium nitrate, or in a protective atmosphere, such as Argon gas, for about 10 seconds to 60 minutes. In this embodiment, the heat treated core wire 226 may not be quenched but preferably cooled down to room temperature in a protective atmosphere. This heat treatment imparts superelastic characteristics to the core wire. Heat treatments below 750° C. do not result in heavy oxidation and therefore may be performed in air.

Figure 7C:
FIG. 7C is a schematic view of a third process step for producing the core wire.

Step three in the process shown in FIG. 7C provides the core wire 226 with a tapered configuration toward its distal end. The tapering of the wire may be produced by a centerless grinding technique or similar method as would be known to one skilled in the art. In one preferred embodiment, for a core wire with a length of about 37 mm, the wire 226 may be tapered over a distance of about 30 mm.

Figure 7D:
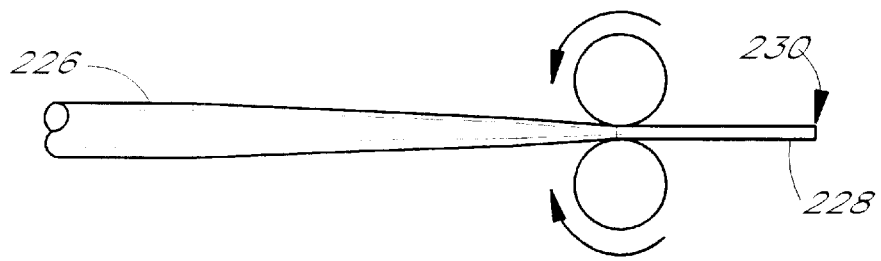
FIG. 7D is a schematic view of a fourth process step for producing the core wire.

The fourth step of the process shown in FIG. 7D is to remove the superelasticity from the distal end of the core wire by providing an additional cold work at the distal end 230. This cold work is preferably performed by rollers to produce a flattened tip 228 at a length about 5–10 mm from the distal end 230, and more preferably for a length of about 7.5 mm. The preferred cold work range is between about 10 and 50%, and more preferably about 40%. Alternate means for cold working the distal end of the core wire may be used, such as wire drawing or neutron radiation, or other means that would be known to those skilled in the art. As a result of the cold working, the nitinol core wire deforms to a cold worked martensite phase.

As shown in FIG. 8A, the core wire that results from the above described manufacturing has a constant cross-section from proximal end 248 to a boundary 242, and then tapers in an extending portion 246 from a greater diameter at boundary 242 to a smaller diameter at second boundary 244 towards the distal end 230 of the wire 226. The cross-sectional area of extending portion 246 decreases by at least about 20%, preferably by at least about 60%, more preferably by about 70%, and optimally by about 80% or more. In one embodiment, the core wire has a diameter of about 0.075 inches at boundary 242 and a diameter of about 0.003 inches at boundary 244. Beyond boundary 244, a region of constant cross-section 228 is provided where the core wire has a planar configuration, as shown in FIG. 8B. This flattened, constant cross-sectional area preferably has a length of between about 5 and 10 mm, and more preferably a length of about 7.5 mm. The thickness of the tip is preferably in the range of about 0.001 to 0.004 inches, and more preferably, about 0.002 inches.

As shown in FIG. 8A, the core wire 226 has a proximal section extending from proximal end 248 to the boundary 244 between the tapered section 246 and the flattened tip region 228 which is superelastic. The core wire 226 has a distal section with a flattened tip portion 228 exhibiting no superelasticity. Elastic characteristics of the nitinol alloys can be best viewed by the stress strain diagrams obtained from various mechanical testing methods such as tensile tests, torsion tests, bending tests or compression tests. Among these methods, the tensile test emerges as the most common mechanical testing method. In particular, tensile tests provide very useful information about both the type of deformation and the amount of deformation that a test sample undergoes under an applies stress. In this respect, FIG. 9, which shows the stress-strain relationship of the proximal and distal sections of core wire 26, provides very valuable information about the deformation characteristics of the nitinol alloy under tensile test conditions.

Figure 9:
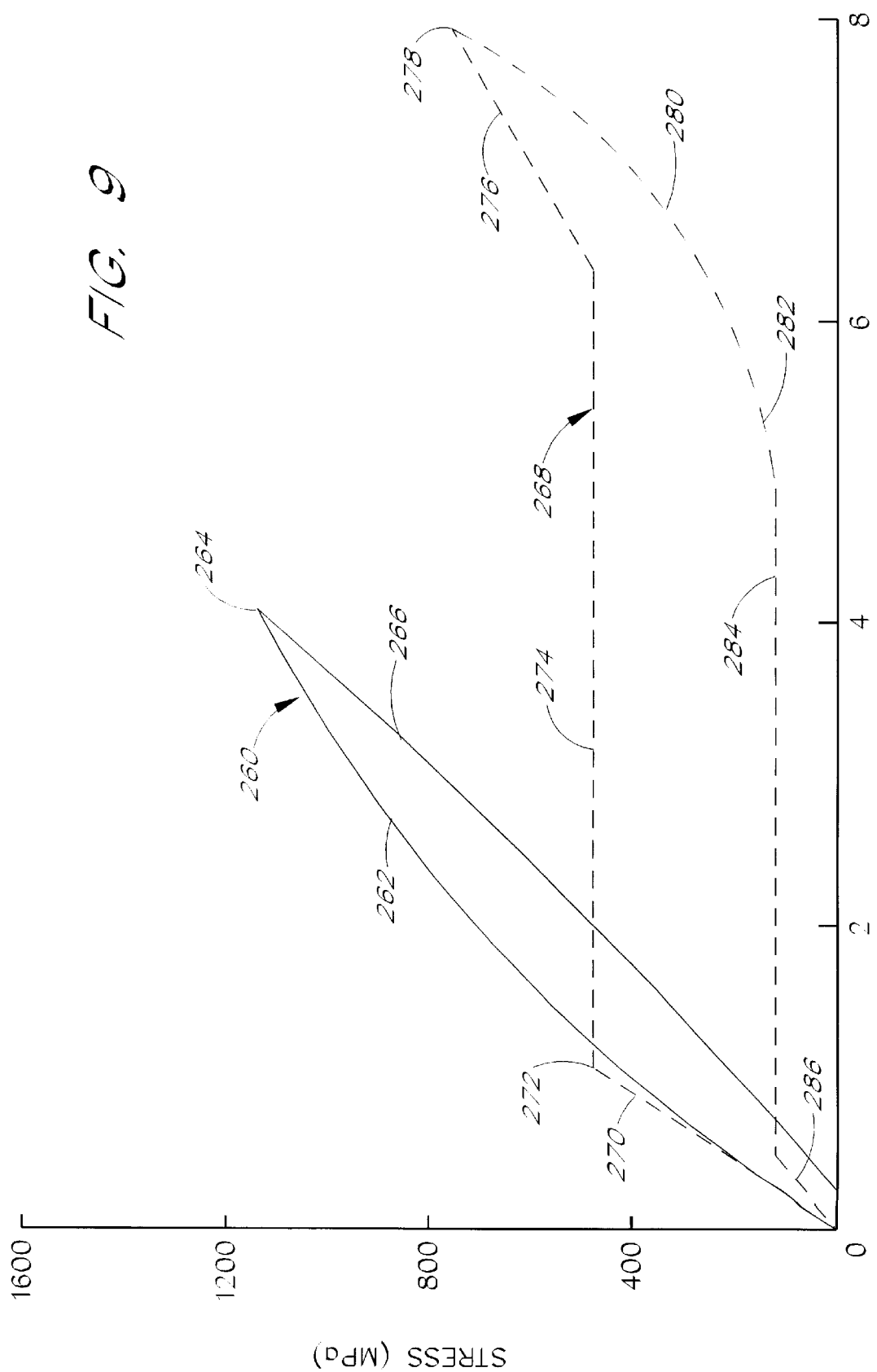
FIG. 9 is a graph comparing the elastic characteristics at the proximal end and at the distal tip of the core wire.

As shown in FIG. 9, the core wire 226 in general exhibits two different types of elastic deformation characteristics. The first deformation characteristics is shown by the solid curve 260, corresponding to the stress-strain behavior of the distal tip 228. Under the applied stress the curve 260 follows a substantially linear path 62, wherein the material elastically deforms up to a point 264, and upon unloading follows a substantially linear unloading curve 266. There is a slight non-linearity in loading and unloading which causes a hysteresis in strain. The material at the tip 228 can thus be deformed to about 4% with less than about 0.3% permanent set.

FIG. 9 also shows a stress-strain curve 268 of the proximal section of the core wire 226. Under the applied stress the curve 268 follows a substantially linear path 270 where the austenitic phase elastically deforms. The austenitic phase elastically deforms with increasing stress up to a critical yielding stress value 72 where martensitic transformation begins. After this critical stress point 272, the material continues to transform into martensite. Throughout the transformation, despite a constant increase in deformation rate of the material, the applied stress remains about the same critical stress value 272 thereby revealing the superelastic property of the material. This superelastic behavior forms a loading plateau 274 on the curve 268 until the entire austenite phase transforms into the martensite phase.

Still referring to FIG. 9, at the end of transformation, the curve 268 no longer follows a straight path but a linearly increasing path 276 where the martensitic material elastically deforms up to a point 278 where unloading begins. During the unloading, the martensite structure transforms into austenite structure. Due to internal friction, there is not an overlap of loading and unloading, and the unloading curve moves down to lower stress values. During the course of unloading, the martensitic phase is first unloaded along the substantially linear portion 280 of curve 268. At a critical stress value 282, martensite to austenite transformation begins and continues along the unloading plateau 284. Upon completion of austenitic transformation, the elastic deformation on austenitic material is unloaded along the linear portion 286.

Thus, the core wire that results is substantially flexible in a proximal section and has less flexibility, and thus, greater shapeability, at a distal tip. In one preferred embodiment, the flexibility in the proximal section results from the material being processed to exhibit transformational superelasticity, i.e., having an austenite phase which will transform to a martensite phase upon the application of stress. The shapeability of the distal section results from the fact that the distal tip 228, because of processing as described above, is in a martensitic phase, and thus exhibits only substantially linear elasticity.

Other processing than the steps described above may be used to impart flexibility and shapeability to the different portions of core wire 226. For instance, instead of cold working and heat treating the wire as shown in FIGS. 7A and 7B, the core wire can be made superelastic by a solution treatment followed by aging process. Solution treatment temperatures are preferably above about 500° C., more preferably above about 700° C., and in one preferred embodiment, about 750° C. Following solution treatment, the core wire is quenched followed by aging. Aging temperatures are preferably in the range of about 300° to 500° C., and more preferably about 350° C.

In addition, superelasticity can be removed from the distal end of core wire 26 by providing an additional heat treatment on the distal end. The heat treatment can be performed with or without need for the second cold work step described in FIG. 7D. The heat treatment preferably occurs at a temperature between about 400° and 800° C. For a temperature of 400° C., a heat treatment for about an hour or more is necessary to remove superelasticity from the core wire. For a temperature of 800° C., a heat treatment for about ten minutes or more will remove superelasticity. Other combinations of temperature and time of heat treatment to remove superelasticity from the wire as would be known to those skilled in the art. The resulting material at the distal end is in a martensite phase having substantially linear elasticity.

Furthermore, the processing steps described above are not only applicable to core wires. Thus, medical wires and catheters that are either solid or hollow may also be processed using the above techniques to achieve a product that is superelastic in one portion and nonsuperelastic in another.

Securing the Core Wire to the Tubular Body

Figure 10:
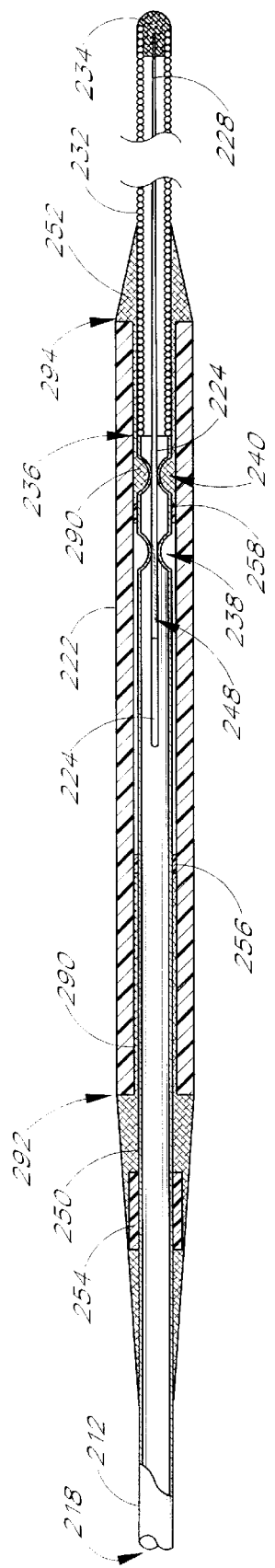
FIG. 10 is a longitudinal cross-sectional view of a distal portion of the catheter implementing the preferred core wire after balloon mounting.

Referring again to FIG. 6, and also to FIG. 10 showing a cross-section of the assembled distal end of catheter 210, there is depicted tubular body 212 incorporating a core wire manufactured by the preferred embodiment of the present invention. The catheter 210 shown in FIG. 10, in addition to showing the tubular body 212, core wire 226 and coil 232 as shown in FIG. 6, also depicts the balloon 222 mounted on the tubular body 212. A distal marker 254 is located on tubular body 212 under an adhesive taper 250 adjacent the proximal end 292 of balloon 222. A distal adhesive taper 252 is provided adjacent the distal end 294 of balloon 222. Other details not necessary to repeat here may be found in the above-referenced application SHAFT FOR MEDICAL CATHETERS, application Ser. No. 09/026,105, filed Feb. 19, 1998, now U.S. Pat. No. 6,288,072.

In order to attach the core wire 226 to the tubular body 212, the coil 232 is first attached to the core wire 226 in a subassembly. The core wire 226 is processed as described above and cut to the desired length. In the embodiment shown in FIGS. 6 and 10, the length of the core wire is about 37 mm. The coil 232 is then cut to a desired length which is shorter than the length of the core wire. As shown in FIGS. 6 and 10, the coil length is about 35 mm. The coil 232 is then slid over the core wire into a position leaving a proximal end 248 of the core wire exposed. In the embodiment shown in FIGS. 6 and 10, the proximal end 248 of the core wire 226 is exposed about 2 mm. The coil 232 is then soldered to the core wire 226, preferably at two positions on the core wire 226. FIG. 6 shows a proximal solder 288 at an intermediate position on the core wire, and a distal solder which forms the ball 234 at distal end 230. Other locations for soldering the coil 232 to the core wire 226 are also contemplated by the invention.

This core wire-coil subassembly is then ready for insertion into tubular body 212. Proximal end 248 of core wire 226 is inserted into a lumen 218 of tubular body 212 until the coil 232 butts against tubular body 212, and core wire 226 is visible through notch 224. Core wire 226 is secured within lumen 218 by crimping tubular body 212 such that the interior surface of tubular body 212 defining lumen 218 contacts proximal end 248 and firmly secures it within lumen 218. Preferably, tubular body 212 is crimped at at least two points to secure proximal end 248 within lumen 218. As shown in FIG. 6, two crimps 238 and 240 secure the tubular body 212 to the come wire 226. In those embodiments where tubular body 212 is made of nitinol, sufficient crimping pressure must be exerted upon tubular body 212 to overcome the elastic response of nitinol. Generally, this requires exertion of sufficient pressure to deform the nitinol tubular body 212 by about 9% or more. For a nitinol tubular body 212 having an outer diameter of 0.014 inches, and an inner diameter of about 0.0095 inches, to be crimped over a nitinol core wire end 248 having an outer diameter of about 0.009 inches, it has been found that a pressure of about 120 ksi is sufficient. Other pressures may also be used provided that they are sufficient to cause tubular body 212 to securely contact core wire 226, but not so great as to unduly deform tubular body 212.

End 248 may be further sealed by use of adhesives 290 which are used to seal the balloon 222 to tubular body 212.

As shown in FIG. 6, balloon 222 is sealed at a proximal end 292 to the tubular body 212, and at a distal end 294 to the coil 232 and tubular body 212. The balloon 222 is bonded to tubular body 212 and the coil 232 by the adhesive 290, preferably a cyanoacrylate such as LOCTITE 4011, although other types of adhesives may be used. The adhesive 290 is applied to the proximal and distal ends 292 and 294 of the balloon 222 and wicks into the balloon 222 up to the position of the adhesive stops 256 and 258. Other details not necessary to repeat here may be found in the above-referenced application BALLOON CATHETER AND METHOD OF MANUFACTURE, application Ser. No. 09/026,225, filed Feb. 19, 1998. This adhesive 290 acts not only to seal the balloon to the catheter, but also to aid in sealing the coil 232 to the distal end 236 of tubular body 212.

Multiple Tapered Core Wire

In another embodiment of the present invention, a core wire is provided having multiple tapers to improve the flexibility and structural properties of a balloon catheter guidewire. As shown in FIGS. 11A and 11B, a balloon catheter 300 is preferably made of a nitinol tubular body 312 such as constructed above having a proximal end 314 (not shown) and a distal end 316 and a lumen 318 extending therethrough. A balloon 322 is mounted to the distal end 316 of the tubular body, preferably such that both the proximal end 322A and distal end 322B of the balloon are both mounted to the tubular body 312. The balloon 322 is preferably made of a compliant C-Flex material as described above, having a length of about 8 mm. A core wire 328 is provided inside the lumen 318 at the distal end 316 of the tubular body and extends distally therefrom. Coils 332 extend from the distal end 316 surrounding core wire 328, and terminate in a distal ball 334.

The tubular body preferably receives cuts 352 to give the hypotube a coiled configuration. A sleeve 366 is preferably provided over the tubular body 312 and cuts 352 at the proximal end of the balloon to prevent inflation fluid from escaping the lumen 318. Adhesive stops 338 and 340 are provided about 2 mm from the ends of the balloon, as described above, to control the wicking length of the adhesive 336 into the balloon working area. Balloon inflation is provided through the cuts in the tubular body 312. A marker 342 is mounted to the tubular body 312 proximal of the balloon 322. Adhesive tapers 344A, 344B and 346 are provided adjacent the balloon to provide a transition region between the tubular body 312 and balloon 322 at the proximal end 322A and between the balloon 322 and the core wire 328 at the distal end 322B. Other details regarding this balloon catheter may be found in assignee's copending application entitled FLEXIBLE CATHETER, application Ser. No. 09/253,591, filed Feb. 22, 1999, the entirety of which is hereby incorporated by reference.

In constructing the catheter 300 of the preferred embodiment, after the tubular body 312 is cut into the desired configuration, the core wire 328 is prepared for mounted inside the distal end 316 of the tubular body 312 as shown in FIG. 1A. The preferred core wire 328 is made of a nitinol material and has a proximal end 328A (not shown) and a distal end 328B. As shown in FIGS. 12A–12D, this core wire 328 preferably has five sections: a proximal first section 370 having a substantially constant diameter, a tapered second section 372, a third section 374 having a substantially constant diameter, a tapered fourth section 376 and a fifth section 378 having a flattened distal tip. As illustrated in FIG. 12A, for the preferred embodiment, the first section 370 preferably has a diameter of about 0.005 to 0.006 inches and a length of about 10 mm. The second section 372 is tapered over a length of about 6 mm, and increases in diameter from about 0.005 to 0.006 inches to about 0.007 inches. The third section 374 has a substantially constant diameter of about 0.007 inches and a length of about 4 mm. The distal end of this third section aligns with the distal end 316 of tubular body 312. The fourth section 376 tapers over a length of about 13 to 15 mm to flattened tip 378, which has a length of about 10 mm and a thickness of about 0.002 inches. Within section 378, an additional taper is provided at transition 380 such that the flat distal tip decreases proximally in thickness to provide a more gradual transition between the thin flat section 378 and the round tapered section 376. This transition 380 preferably has relatively flat surfaces and a length of about 3 to 5 mm.

It should be appreciated that core wires having differing lengths and constructions may also be used for the catheter 300. Thus, a core wire may be provided having only one of the proximal or distal tapers, multiple proximal and distal tapers, or no taper at all. Furthermore, the core wire 328 may be provided without first and second sections 370 and 372 such that substantially all of the core wire 328 extends out of the distal end 316. Moreover, a core wire may be provided having a proximal taper directly adjacent a distal taper.

As described above, the core wire 328 of the preferred embodiment can be manufactured by facilitating various thermal and/or mechanical treatments. The alloy can be made superelastic by cold working the material and then heat treating the alloy. Various facilitating instruments such as swager, metal extrusion and drawing equipment can be utilized to provide cold work. In the preferred embodiment, the core wire 328 is shaped by wire drawing the material at a preferred cold work range of about 20–40% to produce a substantially constant diameter of about 0.007 inches.

Following the cold work the core wire is preferably heat treated as described above to impart superelastic characteristics to the core wire. Tapering of the core wire 328 in sections 372 and 376 is then accomplished preferably by a centerless grinding technique or similar method as would be known to one skilled in the art. The proximal section 370 having a substantially constant diameter is also preferably constructed using centerless grinding.

The distal tip 378 of the core wire is made shapeable by removing its superelasticity as described above. In the preferred embodiment, an additional cold work is provided to the distal end 328B of the core wire using rollers to produce the flattened tip 378. As shown in FIG. 12A, after formation of the flattened tip 378, an additional taper 380 is provided between the tip 378 and the distally tapered section 376. This taper 380 creates a core wire with a smoother transition around the shapeable tip to improve the overall accessibility of the device into blood vessels.

Preferably, the coils 332 are soldered to the core wire and extend from the start of the distally tapered section 376 to the distal end of the flattened tip 378. Thus, for the core wire of the preferred embodiment, the coils 332 extend over a length of about 25 mm. After constructing this coil/core wire subassembly, the core wire 328 is inserted into the lumen 318 of the tubular body 312 such that the beginning of the distal taper in section 376 corresponds with the very distal end 316 of the tubular body and the coils 332 butt against the distal end 316. The core wire 328 is preferably attached to the tubular body 312 in middle section 374 by crimping at one or more points, more preferably at points 362 and 364 as shown in FIG. 11A. Crimping of the tubular body 312 to the core wire 328 can be accomplished using crimping pressures of about 120 ksi or other pressures, as described above. In addition to or in place of crimping, the core wire 328 may also be attached to the tubular body 312 by soldering, adhesives or epoxy, or by any other methods known to one skilled in the art.

The core wire 328 extends proximally into the tubular body 312 through the area where the hypotube is cut. The length that the first, second and third sections 370, 372 and 374 extend into the tubular body 312 is preferably between about 10 and 100 mm, more preferably about 15 to 60 mm, and in the preferred embodiment illustrated in FIG. 11A and 12A, about 20 mm. The length that the core wire 328 extends out of the lumen 318 is preferably about 10 to 200 mm, more preferably about 15 to 60 mm, and as illustrated in FIG. 11A, about 25 mm. By extending the core wire proximally into the hypotube, the core wire provides additional structural support to the catheter. However, because the preferred core wire is proximally tapered, the core wire 328 does not contact the inner wall of the tubular body 312, and therefore, does not substantially interfere with the ability of the catheter to traverse turns in a blood vessel or with the inflation of the balloon.

It will be appreciated that certain variations in the core wire of the present invention and its method of manufacture may suggest themselves to those skilled in the art. The foregoing detailed description is to be clearly understood as given by way of illustration, the spirit and scope of this invention being limited solely by the appended claims.

What is claimed is:

1. A catheter, comprising:
    a tubular body having a proximal end and a distal end, the tubular body having a lumen extending therethrough, and the lumen having a distal end;
    an expandable member mounted on the distal end of the tubular body, the expandable member having a proximal portion and a distal portion which are both mounted to the tubular body; and
    a core wire having a proximal end mounted inside the distal end of the lumen and an extending portion which extends past the distal end of said lumen, the distal end of the tubular body being crimped on the proximal end of the core wire.

2. The catheter of claim 1, wherein the core wire is tapered over a length of no more than 50 mm but at least 15 mm.

3. The catheter of claim 2, wherein the core wire comprises nitinol.

4. The catheter of claim 1, wherein the expandable member comprises an inflatable occlusion balloon.

5. The catheter of claim 1, wherein the core wire is tapered from a first cross-sectional area to a second cross-sectional area, the first cross-sectional area being greater than the second cross-sectional area by at least 20%.

6. The catheter of claim 5, wherein the first cross-sectional area is greater than the second cross-sectional area by at least 70%.

7. The catheter of claim 1, wherein the extending portion has a region of constant cross-sectional area.

8. The catheter of claim 1, where the core wire comprises stainless steel.

9. A hollow guidewire, comprising:
    a nitinol hypotube having a proximal end and a distal end, the hypotube having a lumen extending between the proximal and distal ends;
    an expandable member mounted on the distal end; and
    a metallic core wire inserted into the lumen at the distal end of the nitinol hypotube, the distal end being crimped on the core wire to secure it within the lumen.

10. A catheter, comprising:
    a tubular body having a proximal end and a distal end, the tubular body having an irrigation lumen extending therethrough;
    an irrigation opening on the distal end of the tubular body, the irrigation opening being in fluid communication with the irrigation lumen; and
    a core wire having a proximal end crimped within the lumen and having an extending portion which extends from the distal end of the tubular body, the extending portion being tapered through a length of no more than 60 mm but at least 5 mm.

11. The hollow guidewire of claim 9, wherein the distal end of the hypotube is crimped on the core wire at at least two locations to secure the core wire within the lumen.

12. A catheter, comprising:
    a metallic hypotube having a proximal end and a distal end, wherein the distal end of the tubular body is comprised at least in part of a nitinol alloy;
    an expandable device on the distal end of the tubular body; and
    a metallic core wire mechanically fastened to the distal end of the metallic tubular body, the core wire having an extending portion which extends past the distal end of the tubular body and past the expandable device;
    wherein the distal end of the tubular body is crimped to the metallic core wire.

13. A catheter, comprising:
    a metallic hypotube having a proximal end and a distal end, the hypotube having a lumen extending between the proximal and distal ends;
    an expandable member mounted on the distal end; and
    a metallic core wire attached to the distal end of the hypotube, the core wire having a proximal end and a distal end, the distal end of the core wire extending past the distal end of the hypotube, the distal end of the hypotube being crimped to the core wire to secure the core wire to the hypotube.

14. The catheter of claim 13, wherein the core wire is inserted inside the lumen of the hypotube.

15. The catheter of claim 13, wherein the expandable member has a proximal end and a distal end that are both mounted to the hypotube.

16. The catheter of claim 13, wherein the hypotube is made of nitinol.

17. The catheter of claim 13, wherein the core wire is made of nitinol.

18. The catheter of claim 1, wherein the proximal end of the tubular body has a first wall thickness and the distal end of the tubular body has a second wall thickness, the first wall thickness being greater than the second wall thickness.

19. The catheter of claim 18, wherein the first wall thickness is at least 20% greater than the second wall thickness.

* * * * *

UNITED STATES PATENT AND TRADEMARK OFFICE
CERTIFICATE OF CORRECTION

PATENT NO. : 6,355,016 B1
DATED : March 12, 2002
INVENTOR(S) : Bagaoisan et al.

It is certified that error appears in the above-identified patent and that said Letters Patent is hereby corrected as shown below:

<u>Title page,</u>
Item [75], Inventors, change "Celso J. Bagaoisan, Union City; Ketan P. Muni, San Jose; Gholam-Reza Zadno-Azizi, Newark; Sivette Lam, San Jose; Juan T. Domingo, Union City; Isaac J. Kim, San Jose; Samuel L. Omaleki, Morgan Hill; Jefferey C. Bleam, Boulder Creek, all of CA (US)" to -- Celso J. Bagaoisan, Union City; Ketan P. Muni, San Jose; Gholam-Reza Zadno-Azizi, Newark; Juan T. Domingo, Union City; Isaac J. Kim, San Jose, all of CA (US) --

Signed and Sealed this

Twenty-fourth Day of September, 2002

Attest:

Attesting Officer

JAMES E. ROGAN
*Director of the United States Patent and Trademark Office*